US006326025B1

(12) United States Patent
Sigler et al.

(10) Patent No.: US 6,326,025 B1
(45) Date of Patent: Dec. 4, 2001

(54) TISSUE REACTIVE ADHESIVE COMPOSITIONS

(75) Inventors: Gerry Sigler; Z. David Deng; Dale R. Peterson, all of Carmel; Todd P. Glancy, Fairmount, all of IN (US); Samuel I. Stupp, Evanston, IL (US)

(73) Assignee: DePuy Orthopaedics, Inc, Warsaw, IN (US)

( * ) Notice: Subject to any disclaimer, the term of this patent is extended or adjusted under 35 U.S.C. 154(b) by 0 days.

(21) Appl. No.: 09/530,172

(22) PCT Filed: Dec. 30, 1998

(86) PCT No.: PCT/US98/27854

§ 371 Date: Apr. 24, 2000

§ 102(e) Date: Apr. 24, 2000

(87) PCT Pub. No.: WO99/33419

PCT Pub. Date: Jul. 8, 1999

Related U.S. Application Data

(63) Continuation of application No. 60/070,238, filed as application No. PCT/US98/27854 on Dec. 30, 1998.

(51) Int. Cl.$^7$ ............ A61F 13/02; A61F 31/34; C08F 28/06; C08F 34/04; C08F 128/04
(52) U.S. Cl. ............ 424/444; 424/484; 514/438; 514/441; 526/256; 602/42; 602/43; 602/48; 602/50; 602/904; 606/213
(58) Field of Search ............... 424/444, 484; 514/438, 441; 526/256; 602/42, 43, 48, 50, 904; 606/213, 214

(56) References Cited

U.S. PATENT DOCUMENTS 5,412,076 * 5/1995 Gagnieu .................. 530/356
5,582,834 * 12/1996 Leung et al. .............. 424/426

* cited by examiner

*Primary Examiner*—Nathan M. Nutter
(74) *Attorney, Agent, or Firm*—Barnes & Thornburg

(57) ABSTRACT

The present invention is directed to a biocompatible tissue reactive composition comprising a functionalized polymer having tissue reactive substituents that are capable of forming covalent bonds with tissue associated functional groups.

20 Claims, No Drawings

TISSUE REACTIVE ADHESIVE COMPOSITIONS

CROSS-REFERENCES TO RELATED APPLICATIONS

This application is a U.S. national application of international application serial No. PCT/US98/27854 filed Dec. 30, 1998, which claims priority to U.S. provisional application serial No. 60/070,238 filed Dec. 31, 1997.

FIELD OF INVENTION

The present invention relates to a biocompatible tissue reactive adhesive composition and a method of repairing damaged tissue. More particularly this invention is directed to a biocompatible tissue reactive composition comprising a functionalized polymer having tissue reactive substituents that are capable of forming covalent bonds with tissue associated functional groups.

BACKGROUND AND SUMMARY OF THE INVENTION

With the advent of rapid advances in surgical techniques and the development of new biocompatible materials for prosthetic implants, researchers have also focused their attention on development of new tissue/implant fixation techniques. One facet of such research has been the formulation of surgical adhesives that can be used as a substitute for, or in combination with, standard mechanical fixation techniques. Recently biocompatible adhesives for surgical use have been proposed based, at least in part, on what has been learned about natural bioadhesives, for example, the proteinaceous compositions produced by barnacles that allow that species to attach themselves with seemingly permanent fixation to a wide variety of underwater structures. Much has been learned about the "chemistry" of such natural adhesives, and efforts are being made to harness such chemistry for production of glues and adhesives for use in surgical applications.

The present invention is based on the use of "chemistry", albeit different from the chemistry of marine-derived natural adhesives, to optimize adhesive function under physiological conditions. More particularly, the invention is based on the reactivity of certain polymer-associated functional groups with tissue-associated functional groups. The adhesive composition reacts with and forms covalent bonds with tissue in vivo. The functional groups on the adhesive polymer components of the present composition are selected such that upon reaction with functional groups on the molecular components of tissue, there is propagated a second reactive functional group that can in turn react intramolecularly or intermolecularly with at least one other functional group on the adhesive polymer to effect covalent crosslinking and "setting" of the adhesive in vivo.

Thus in accordance with one embodiment of the invention there is provided a tissue-reactive adhesive composition comprising a biocompatible polymer substituted with at least one tissue reactive functional group.

In another embodiment the substituted biocompatible polymer is combined with a monomer or oligomer having at least a tissue reactive substituent and a thiol-reactive substituent to form the tissue-adhesive composition.

In another embodiment of this invention the tissue-adhesive composition further comprises effective amounts of one or more biologically active components to form a self-adhesive implant capable of providing sustained release of the biologically active component in vivo.

In another embodiment of this invention the tissue-reactive adhesive composition can be utilized alone or in combination with mechanical fixation techniques as a surgical glue for adjoining tissue surfaces or for fixation of prosthetic implants.

DETAILED DESCRIPTION

This invention provides a tissue-adhesive composition that comprises a biocompatible polymer bearing covalently bound tissue-reactive substituent groups. In one embodiment, the covalently bound tissue-reactive substituent group includes a thiolactone group of the formula

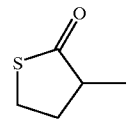

That group reacts under physiologic conditions with tissue-associated hydroxy, amino and thiol groups to form the corresponding acyclic esters, amides and thiol esters respectively, with concomitant production of an acyclic thiol moiety. In another embodiment, the biocompatible polymer component of the present tissue-adhesive composition includes a tissue reactive substituent comprising a boronic acid functional group of the formula —B(OH)$_2$. That functional group reacts under physiological conditions with tissue-associated hydroxyl groups, particularly vicinal dihydroxy functional groups, to form cyclic boronate esters. In one preferred embodiment of this invention the biocompatible polymer component of the present tissue-adhesive composition also includes a thiol-reactive substituent that comprises a divalent group of the formula —CR=CR'— or —C≡C— wherein R and R' are independently hydrogen or optionally substituted C$_1$–C$_6$ alky. The thiol-reactive substituent including such divalent olefinic or acetylenic group can be cyclic or acyclic. The structure of such thiol-reactive groups is not critical provided that they exhibit reactivity with thiol functionalities under physiologic conditions to form the corresponding sulfides. The reaction of a thiol moiety with the thiol-reactive substituents work, in the case of tissue-associated thiol groups, to covalently bond the polymer component of the adhesive composition to tissue. Such sulfide formation can also occur intra- or intermolecularly in the adhesive composition, for example, between thiol-reactive polymer bound substituents and thiol groups released upon hydrolysis, alcoholysis, aminolysis or thiolysis of the polymer bound thiolactone groups to effectively crosslink the polymer component of the tissue-adhesive composition post implant.

The inherent tissue compatibility of the biocompatible polymer component of the present adhesive composition is optimized where the polymer is selected to include or is chemically modified to include, in addition to the tissue reactive and/or thiol-reactive substituents, substituent groups that are substantially cationic at physiological pH, including groups such as amino, amidino, and guanidino. The resultant cationic character of the biocompatible polymer in vivo allows, indeed promotes, compatibility/affinity with to endogenous tissue which is recognized to have aggregate anionic character.

The tissue-adhesive compositions of this invention rely for their efficacy on their capacity to react with and covalently bond to tissue in vivo, and in certain embodiments, to undergo post-implant crosslinking which works to strengthen the adhesive and cohesive properties of the composition after implantation without free-radical based chemistry or the production and concomitant release of undesirable chemical byproducts. The tissue-adhesive composition can be used to bond and repair adjoining tissue surfaces, or it can be used alone or in combination with mechanical fixation techniques as a surgical glue for fixation of prosthetic implants. Alternatively, the adhesive composition of the present invention can be combined with one or more biologically active compounds, for example, antibiotics, anti-inflammatories, growth factors and the like and used to form a self-adhesive implant capable of providing sustained release of the biologically active component in vivo.

One key component of the tissue-adhesive composition of this invention is a biocompatible polymer having one or more, preferably multiple, covalently bound substituent groups capable of reacting with tissue associated hydroxy, amino, carboxy and thiol functional groups. It is important that the reactive polymer components of the present tissue-adhesive compositions are biocompatible and that they are non-toxic, non-immunogenic and elicit minimal inflammatory responses in vivo. Otherwise, the nature of the polymer is not critical, except that it have the specified functional groups or other pendent functional groups that can be chemically modified to provide the above-mentioned tissue-reactive or thiol-reactive substituent groups. The intermediate polymer (the polymer "backbone") which is chemically modified to form the polymer component of the present adhesive composition can be in the form of a homopolymer, terpolymer, copolymer, block copolymer, or a polymer blend. The polymers can be biodegradable or non-biodegradable, but bioerodible, i.e., partially soluble in physiological fluids. Examples of biodegradable polymers that they be used to prepare the substituted polymer components of the present tissue-adhesive compositions include polyanhydrides, polyesters including polylactic acid, polyglycolic acid, copolymers of lactic and glycolic acid alone or in combination with caproic acid, and poly(arnino) acids. Examples of other polymer types to be used in preparing the substituted polymer components of the present tissue-adhesive composition include polyhydroxyethyl methacrylate, polymethyl methacrylate, polyacrylic acid, and polyethylene glycol copolymers such as a copolymer formed with ethylene oxide and 4,5-epoxy pentanoic acid sold under the trade name Pendant Poly(ethylene glycol)-propionic acid by Shearwater Polymer, Inc. In one embodiment, the intermediate polymer is selected so that the reactive substituent-bearing polymer derivatives used in the tissue-adhesive composition are moldable by hand at temperatures between about 0° and 60° C. The substituent polymer bearing components of the present composition will typically have a glass transition temperature ($T_g$) of less than about 90° C.; in one embodiment the substituted biocompatible polymer component has a glass transition temperature of less than about 40° C. In another embodiment the substituted biocompatible polymer has a glass transition temperature from about 40° to about 90° C. The polymer component of the present tissue compositions typically have a molecular weight of about 1500 to 50,000 Daltons, more typically about 1800 to about 20,000 Daltons.

The polymer component of the tissue-adhesive composition of this invention is selected or prepared to have one or more covalently bound tissue reactive substituent groups. In one embodiment the tissue reactive substituent groups are selected from a thiolactone of the formula

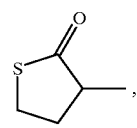

a boronic acid group of the formula —B(OH)$_2$, and a thiol-reactive unsaturated hydrocarbyl substituent. Such substituted polymers can be prepared either by forming said polymers from monomeric components including such substituents, or by reacting polymer intermediates having functional groups capable of being chemically modified to include one or more of the above-referenced tissue reactive or thiol-reactive substituents. Thus, polymer intermediates can be selected to include, for example, pendent hydroxy or amino functional groups that can be reacted, for example, by alkylation or acylation reactions to covalently couple the polymer to substituent groups comprising the above-mentioned tissue-reactive or thiol-reactive moieties. Alternatively, polymer intermediates having carboxy functionality can be reacted with, for example, ester forming or amide forming compounds including one or more of the above-mentioned tissue-reactive or thiol-reactive functional groups to covalently bind such groups to the polymer for use in the present tissue-adhesive compositions.

Thus, a biocompatible polymer having inter alia a thiol-reactive substituent can be prepared by reacting an intermediate polymer with a compound of the formula H-L$_n$-X wherein H is a thiol-reactive, unsaturated, cyclic or acyclic hydrocarbyl group comprising a divalent group of the formula —CR=CR'— or —C≡C—, wherein R and R' are independently hydrogen or optionally substituted C$_1$–C$_6$ alkyl; L is a linking group, n is 0 or 1, and X is a functional group capable of forming a covalent bond with a functional group on the intermediate polymer. The nature of the linking group L is not critical; it is simply an optional divalent group coupling the thiol-reactive substituent H ultimately to the polymer. The functional group X can represent, for example, a good leaving group, where the polymer component includes nucleophilic groups capable of displacing X and forming a covalent bond through linker-L- to the unsaturated hydrocarbyl group. Alternatively, X can be a carboxy group capable of being activated, for example, by active ester formation, for acylation coupling to hydroxy and/or amino functional groups on the intermediate polymer.

Similarly, tissue-reactive thiolactone substituents can be covalently linked to the polymer utilizing a compound of the formula TL-L$_n$-X wherein TL represents the thiolactone moiety, and L, n and X are as defined above. Boronic acid substituents can be linked to the polymer through similar reactive intermediates.

The degree of substitution with the tissue-reactive and thiol-reactive substituents on the biocompatible polymer can vary widely and can be selected to provide the desired use-dependent adhesive properties. The biocompatible polymer component of the present tissue-adhesive composition should include at least one covalently bound tissue-reactive/thiol-reactive thiolactone substituent. Preferably the polymer is also substituted with at least one thiol-reactive unsaturated hydrocarbyl substituent. Optionally it can be substituted as well with one or more boronic acid substituent groups. In another embodiment the biocompatible polymer component of the present tissue-adhesive composition includes multiple covalently bound thiolactone groups and multiple thiol-reactive unsaturated hydrocarbyl groups, and such is optionally further substituted with one or more boronic acid functional groups. Alternatively, the biocompatible polymer component of the present tissue adhesive composition is prepared to include a covalently bound tissue-reactive substituent comprising a boronic acid group, with or without additional tissue-reactive or thiol-reactive substituents.

The present tissue-adhesive compositions can be formulated to include, in addition to the above-mentioned covalently substituted biocompatible polymer, about 1 to about 60% by weight of a monomer or oligomer having at least two covalently bound substituent groups selected from the group consisting of a tissue-reactive substituent comprising a thiolactone group of the formula

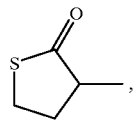

a thiol-reactive unsaturated hydrocarbyl substituent comprising a divalent group of the formula —CR=CR'— or —C≡C— wherein R and R' are independently hydrogen or optionally substituted $C_1$–$C_6$ alky; and a tissue-reactive substituent comprising a boronic acid group of the formula —$B(OH)_2$. Such monomers or oligomers typically have a molecular weight between about 100 and about 1200. The biocompatible polymer component can be blended with the monomer or oligomer to form a solution or suspension which can be applied to the tissue and/or prosthetic surfaces as a surgical glue. Alternatively, tissues to be adjoined and bonded as part of a surgical repair process can be pretreated with the tissue-reactive monomer or oligomer prior to applying the present tissue-adhesive composition comprising the biocompatible multi-functional polymer.

The present tissue-adhesive composition is used alone or in combination with mechanical/tissue fixation repair techniques. Where the tissue-adhesive composition is used alone, the adjoining surfaces are typically coated with the present tissue-adhesive composition, and the surfaces being joined are temporarily held in contact with pressure applied to the bonded tissue for a period of time to initiate covalent linking of tissue-reactive functional groups and the adhesive composition in contact with the adjoining tissue surfaces.

In another embodiment of this invention, the tissue-adhesive composition is formulated to include one or more biologically active ingredients. The adhesive composition so formulated can be used for surgical repair or simply as a bolus implant for sustained release of the biologically active component. The biologically active agents can be selected from a wide variety of art recognized compounds, including classical therapeutic agents such as antibiotics or anti-inflammatory substances, proteins such as a growth factors or cytokines, and DNA or living cells. The proteins can include extracts from cells, serum, skin, bone, and other tissues and can also include cellular or acellular tissue components. Thus, suitable biologically active agents can be extracted from whole blood or components thereof, skin, bone, cartilage, tendon, microorganisms, and the like; the protein components can include synthetic proteins, proteins produced by recombinant DNA techniques, hormones, enzymes, albumin, or structural proteins such as keratins and collagens, and can also include simple proteins or conjugated proteins such as glycoproteins, mucoproteins, lipoproteins, heme proteins, nucleoproteins and the like. DNA components can include, for example, DNA including the sequence encoding for transforming growth factorβ and bone morphogenic proteins that are useful for bone or cartilage regeneration. Examples of growth factors for use in the tissue-adhesive composition of this invention include fibroblast growth factor, transforming growth factor, epidermal growth factor, platelet-derived growth factor, insulin-like growth factor, and the like. Growth factor binding proteins including insulin-like growth factor binding proteins such as IGFBP 3 and 5 can also be used as a component of the present adhesive composition. Examples of cells that can be used in the present tissue-adhesive compositions are bone marrow cells and cartilage cells. Potential osteogenic bioactive components comprise demineralized bone powder, cancellous bone, aspirated bone marrow, bone or cartilage forming cells or their precursors, and the like. Alternatively the present composition can be formulated to include art-recognized pharmaceutical agents such as antibacterial compounds, for example, gentamicin and vancomycin, or steroidal anti-inflammatory substances such as cortisone, hydrocortisone and synthetic prednisolone. Other optional components for the tissue-adhesive composition include extraneous proteins such as gelatin or albumin, and antioxidants such as tocopherol, citric acid, butylated hydroxyanisole, butylated hydroxytoluene, tertiary butylhydroquinone, propyl gallate, ascorbate, and other antioxidants that are "generally recognized as safe" by the Food and Drug Administration.

The tissue-adhesive composition of this invention can be used in surgical procedures to provide temporary fixation for prosthetic implants to damaged or diseased tissue. The adhesive composition is utilized to immobilize the prosthesis for a period of time to allow regrowth of endogenous tissue a concomitant "natural" fixation of the implant structure or mending or healing of adjoined tissues. Thus the present tissue-adhesive composition can be used to secure, for example, "felted" polylactic acid or polyglycolic acid used to provide a temporary matrix structure for the growth of cartilage generating cells for production/regrowth of damaged cartilage structures. The present tissue-adhesive composition allows "covalent" temporary fixation of the implant. The present adhesive composition can be used as a surgical glue for a wide variety of endogenous tissue structures, including skin, cartilage, and bone. When the implanted tissue-adhesive composition includes a biologically active ingredient, the biologically active component, the biologically component is slowly released from the adhesive matrix during a period of time following implantation. Typically, the biologically active agent is selected to facilitate healing at the site of surgical repair or simply to help minimize the probability of unwanted infection (where the biologically active agent is an antibiotic) or inflammation (where the agent is an anti-inflammatory compound). In another surgical application the tissue-adhesive composition containing a biologically active agent can be used to fill a void or other defect in a bone by simply pushing a portion of the composition into the defect and molding it to conform to the defect.

EXAMPLE 1

Preparation of Poly(L-Arginine) Poly(Ornithine) Based Adhesive

All reactions were performed with dry deaerated solvents and reagents under an atmosphere of dry nitrogen. Three equivalents of maleimidopropionic acid N-hydroxysuccinimide ester and three equivalents of triethylamine were added with stirring to a dry dimethyl sulfoxide (DMSO) solution of poly L-arginine hydrochloride (Sigma Chemical Co.; containing from about 1 to about 3% ornithine monomers) at room temperature. After about two hours, dry tetrahydrofuran (THF) was added to the mixture to precipitate the resulting polymer. The polymer was dried under vacuum at room temperature. Efficiency of the reaction between the polyarginine/polyornithine copolymer and the maleimidopropionic acid N-hydroxy succinimide ester was confirmed using trinitrobenzensulfonate, a compound that forms a highly chromogenic complex with free amines, according to the procedure of Ellman (Ellman, Arch. Biochem. Biophys 82, 70, 1959).

The resulting intermediate polymer product was dissolved in dry DMSO, and one equivalent of D,L homocysteine thiolactone hydrochloride (HCTL) and two equivalents of ethyl-3-(3-dimethylamino-propyl)carbodiimide were added with stirring. After about ten minutes, six equivalents of dry pyridine in DMSO were added, and the resulting solution was stirred for about 12–18 hours under an atmosphere of dry nitrogen at room temperature. The resulting functionalized polymer was precipitated with THF, collected and then dried at room temperature at high vacuum.

The polymer product (hereinafter "poly(Arg)-TL") was stored as a dry powder. A gel forms within 10–15 minutes following dissolution o the polymer in water. Gel formation is believed to result from hydrolysis of the thiolactone ring of the homo cysteine thiolactone and subsequent crosslinking of the polymer.

Adhesion characteristics of poly(Arg)-TL were determined by tensile testing according to the following procedure:

Glass slides were cleaned by first immersing them in a hot sulfuric acid bath for 10 minutes. The slides were rinsed thoroughly with ultrapure water. Then they were placed in a warm ammonium hydroxide:hydrogen peroxide (4:1 by volume) bath for 1 minute. The glass slides were again rinsed with ultrapure water, and dried with filtered nitrogen.

Water swollen chondroitin sulfate (CS) was used as a test substrate in order to simulate wet tissue. The cleaned glass slides were pretreated with an amino-silane coating. An aqueous solution of CS was applied to the pretreated glass slides (4.83 cm² exposed surface area). The CS gelled to provide a CS film on the glass slides.

The CS film, cast on glass, was placed in a 100% humidity chamber for 30 minutes before testing. Poly(Arg)-TL was sprinkled onto one of the CS covered glass slides. A second CS covered glass slide was placed on top of the first and the two slides were pressed together with a force of about 15 Newtons for either 30 or 90 minutes. A test device was then used to measure the stress and strain as the two slides are separated at an angle of about 90° relative to the face of the two glass plates The separation speed was 0.5 mm per minute.

The results of the adhesion tests for the poly(Arg)-TL are listed in Tables 1 and 2. The poly(Arg)-TL exhibited significantly greater adhesive strength than the poly(L-arginine)-poly(ornithine) copolymer [poly(Arg)-poly(Orn)] that was not reacted with either maleimidopropionic acid N-hydroxysuccinimide ester or the D,L-homocysteine thiolactone hydrochloride. The adhesion of the poly(Arg)-TL adhesive composition to the CS covered glass slides ranged from 9.4 to 22.59 Newtons. This is in contrast to the poly(Arg)-poly(Orn) that exhibited no adhesive characteristics when tested on CS covered glass slides according to the above procedure.

TABLE 1

Adhesion test of poly(Arg)-TL on swollen CS covered glass slides after performed after 30 minutes at 15 N pressure.

| Test | Amt of pArgTL (mg) | Amt of CS on slide 1 (mg) | Amt of CS on slide 2 (mg) | Max Force (N) | Distance to failure (mm) |
|---|---|---|---|---|---|
| 1 | 4.7 | 10 | 10 | 21.48 | 0.45 |
| 2 | 4.7 | 10 | 20 | 12.39 | 0.33 |
| 3 | 3.8 | 10 | 10 | 12.85 | 0.42 |
| 4 | 8 | 20 | 20 | 14.23 | 0.49 |
| 5 | 13.3 | 35 | 35 | 18.3 | 0.53 |

TABLE 2

Adhesion test of poly(Arg)-TL on swollen CS covered glass slides performed after 90 minutes at 15 N pressure.

| Test | Amt of pArgTL (mg) | Amt of CS on slide 1 (mg) | Amt of CS on slide 2 (mg) | Max Force (N) | Distance to failure (mm) |
|---|---|---|---|---|---|
| 1 | 4.4 | 20 | 20 | 9.4 | 0.48 |
| 2 | 8.2 | 40 | 20 | 13.28 | 0.74 |
| 3 | 5 | 10 | 10 | 22.59 | 0.74 |

EXAMPLE 2

Preparation of Polyethylene Glvcol Based Adhesive

Poly(ethylene glycol)-propionic acid (sold by Shearwater Polymers, Inc.) having a weight average molecular weight of 5000 Da and containing an average of 3.79 propionic acid pendant groups per polymer molecule was dissolved in dimethyl formamide (DMF). DL-homocysteine thiolactone (1.9 equivalents) and 4-(4-N-maleimidophenyl)-butyric acid hydrazide (1.9 equivalents) were added with stirring at room temperature. The resulting mixture was cooled to 0° C., and 7.6 equivalents of ethyl-3(3-dimethylaminopropyl) carbodiimide were added. After thirty minutes, the reaction mixture was allowed to warm to room temperature, and the mixture was stirred for an additional 12 hours at room temperature. The resulting functionalized polymer was precipitated by the addition of diethyl ether; the polymer was collected, and dried under vacuum at room temperature. The dry functionalized polymer was stored in a desiccator until it was used.

What is claimed is:

1. A tissue-adhesive composition comprising a biocompatible polymer including a covalently bound tissue reactive substituent group of the formula

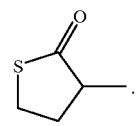

2. The tissue-adhesive composition of claim 1 wherein the biocompatible polymer further includes a covalently bound thiol-reactive substituent comprising a divalent group of the formula —CR=CR'— or —C≡C— wherein R and R' are independently hydrogen or optionally substituted $C_1$–$C_6$ alkyl.

3. The adhesive composition of claim 1 wherein the biocompatible polymer is a polyamino acid, a polyethylene glycol copolymer, a polyester, a polyurethane, a polyacrylic acid, a polyhydroxyethyl methacrylate, or a polymethyl methacrylate.

4. The tissue-adhesive of claim 1 wherein the biocompatible polymer further includes a covalently bound tissue reactive substituent comprising a boronic acid group of the formula —B(OH)$_2$.

5. The tissue-adhesive composition of claim 1 wherein the biocompatible polymer further includes a covalently bound substituent group that is substantially cationic at physiological pH.

6. The tissue-adhesive composition of claim 4 wherein the biocompatible polymer further includes a covalently bound substituent group that is substantially cationic at physiological pH.

7. The tissue-adhesive composition of claim 1 wherein the biocompatible polymer has a glass transition temperature of less than about 40° C.

8. The tissue-adhesive composition of claim 5 wherein the biocompatible polymer has a glass transition temperature from about 40° to about 90° C.

9. The tissue-adhesive composition of claim 1 further comprising about 1 to about 60% by weight of a monomer or oligomer having at least two covalently bound substituent groups selected from the group consisting of a tissue reactive substituent comprising the group of the formula

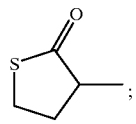

a thiol-reactive substituent comprising a divalent group of the formula —CR═CR'— or —C≡C— wherein R and R' are independently hydrogen or optionally substituted C$_1$–C$_6$ alkyl; and, a tissue reactive substituent comprising a boronic acid group of the formula —B(OH)$_2$.

10. The biocompatible adhesive of claim 1 further comprising a biologically active agent.

11. A tissue-adhesive composition comprising a biocompatible polymer including a covalently bound tissue reactive substituent comprising a boronic acid group of the formula B(OH)$_2$.

12. In a method of repairing tissue using a biocompatible adhesive to bond adjoining tissue surfaces the improvement which comprises selecting, as the biocompatible adhesive, the adhesive composition of claim 1.

13. The method of claim 12 further comprising the step of pretreating the adjoining tissue surface with a monomer or oligomer having at least two covalently bound substituent groups, one of which is a tissue reactive substituent comprising a boronic acid group of the formula —B(OH)$_2$ and the other selected from the group consisting of a tissue reactive substituent comprising a group of the formula

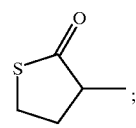

and a thiol-reactive substituent comprising a divalent group of the formula —CR═CR'— or —C≡C— wherein R and R' are independently hydrogen or optionally substituted C$_1$–C$_6$ alkyl.

14. The adhesive composition of claim 2 wherein the biocompatible polymer is a polyamino acid, a polyethylene glycol copolymer, a polyester, a polyurethane, a polyacrylic acid, a polyhydroxyethyl methacrylate, or a polymethyl methacrylate.

15. The tissue-adhesive of claim 2 wherein the biocompatible polymer further includes a covalently bound tissue reactive substituent comprising a boronic acid group of the formula —B(OH)$_2$.

16. The tissue-adhesive composition of claim 2 wherein the biocompatible polymer further includes a covalently bound substituent group that is substantially cationic at physiological pH.

17. The tissue-adhesive composition of claim 15 wherein the biocompatible polymer further includes a covalently bound substituent group that is substantially cationic at physiological pH.

18. The tissue-adhesive composition of claim 16 wherein the biocompatible polymer has a glass transition temperature from about 40° to about 90° C.

19. The tissue-adhesive composition of claim 2 further comprising about 1 to about 60% by weight of a monomer or oligomer having at least two covalently bound substituent groups selected from the group consisting of a tissue reactive substituent comprising the group of the formula

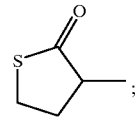

a thiol-reactive substituent comprising a divalent group of the formula —CR═CR'— or —C≡C— wherein R and R' are independently hydrogen or optionally substituted C$_1$–C$_6$ alky; and, a tissue reactive substituent comprising a boronic acid group of the formula —B(OH)$_2$.

20. The biocompatible adhesive of claim 2 further comprising a biologically active agent.

* * * * *